(12) United States Patent
Marcacci

(10) Patent No.: US 11,166,830 B2
(45) Date of Patent: Nov. 9, 2021

(54) SURGICAL METHOD FOR IMPLANTING A PROSTHESIS IN A PATIENT

(71) Applicant: REJOINT S.r.l., Bologna (IT)

(72) Inventor: Maurilio Marcacci, Bologna (IT)

(73) Assignee: REJOINT S.R.L., Bologna (IT)

( * ) Notice: Subject to any disclaimer, the term of this patent is extended or adjusted under 35 U.S.C. 154(b) by 117 days.

(21) Appl. No.: 16/670,721

(22) Filed: Oct. 31, 2019

(65) Prior Publication Data

US 2021/0128317 A1    May 6, 2021

(51) Int. Cl.
| | |
|---|---|
| *A61B 17/58* | (2006.01) |
| *A61B 17/60* | (2006.01) |
| *A61F 2/00* | (2006.01) |
| *A61F 2/46* | (2006.01) |
| *A61B 34/10* | (2016.01) |
| *A61B 17/17* | (2006.01) |

(52) U.S. Cl.
CPC .......... *A61F 2/461* (2013.01); *A61B 17/1764* (2013.01); *A61B 34/10* (2016.02); *A61B 2034/108* (2016.02)

(58) Field of Classification Search
CPC combination set(s) only.
See application file for complete search history.

(56) References Cited

FOREIGN PATENT DOCUMENTS

FR    2840797 A1 * 12/2003    ........... A61B 17/155

* cited by examiner

*Primary Examiner* — Sameh R Boles
(74) *Attorney, Agent, or Firm* — Knobbe, Martens, Olson & Bear, LLP

(57) ABSTRACT

The disclosure herein relates to various surgical methods for implanting a prosthesis in a patient. In particular, in some embodiments, a surgical method for preparing a knee of a patient to implant a customized knee prosthesis comprising: identifying epiphysary axis (2) of the patient tibia (1) by connecting the center of the tibial plateau with the center of the growth plate remnant on a preoperative planning; and performing a tibial cut (3) perpendicular to the epiphysary axis (2) of the tibia (1).

1 Claim, 2 Drawing Sheets

SURGICAL METHOD FOR IMPLANTING A PROSTHESIS IN A PATIENT

BACKGROUND

Field

The present application relates to surgical methods for implanting a prosthesis in a patient.

Description

Orthopedic procedures and prostheses are commonly used to repair or replace damaged bone and tissue in the human body. The purpose of prosthetic knee surgery is in fact to reduce pain and restore the function of the diseased joint.

SUMMARY

Various embodiments described herein relate to surgical methods for implanting a prosthesis in a patient. In particular, in some embodiments, a surgical method for preparing a knee of a patient to implant a customized knee prosthesis comprising: identifying epiphysary axis (2) of the patient tibia (1) by connecting the center of the tibial plateau with the center of the growth plate remnant on a preoperative planning; and performing a tibial cut (3) perpendicular to the epiphysary axis (2) of the tibia (1). In some embodiments of the surgical method for preparing a knee of a patient to implant a customized knee prosthesis, a cutting guide based on the mechanical axis (8) of the tibia (1) is used and the angle between the epiphysary axis (2) and the mechanical axis (8) of the tibia (1) is measured to perform the tibial cut (3).

In some embodiments, a surgical method for preparing a knee of a patient to implant a customized knee prosthesis comprises: identifying the bisector axis (5) of the trochlear groove (7) of the patient femur (4) on a preoperative planning; and performing the femur cut (6) perpendicular to the bisector axis (5). In some embodiments of the surgical method for preparing a knee of a patient to implant a customized knee prosthesis, a cutting guide based on the mechanical axis (9) of the femur (4) is used and the angle between the bisector axis (5) and mechanical axis of the femur is measured to perform the femur cut (6).

In some embodiments, a surgical method for implanting a customized prosthesis in a knee of a patient comprises the steps of: identifying epiphysary axis (2) of the patient tibia (1) by connecting the center of the tibial plateau with the center of the growth plate remnant on a preoperative planning and then performing a tibial cut (3) perpendicular to the epiphysary axis (2) of the tibia (1); identifying the bisector axis (5) of the trochlear groove (7) of the patient femur (4) on a preoperative planning and then performing the femur cut (6) perpendicular to the bisector axis (5); realizing a patient specific prosthesis on the basis of the performed tibial cut (3) and femur cut (6); and implanting the patient specific prosthesis in the knee of the patient.

For purposes of this summary, certain aspects, advantages, and novel features of the invention are described herein. It is to be understood that not necessarily all such advantages may be achieved in accordance with any particular embodiment of the invention. Thus, for example, those skilled in the art will recognize that the invention may be embodied or carried out in a manner that achieves one advantage or group of advantages as taught herein without necessarily achieving other advantages as may be taught or suggested herein.

All of these embodiments are intended to be within the scope of the invention herein disclosed. These and other embodiments will become readily apparent to those skilled in the art from the following detailed description having reference to the attached figures, the invention not being limited to any particular disclosed embodiment(s).

BRIEF DESCRIPTION OF THE DRAWINGS

Further characteristics and advantages of the invention will more fully emerge from the description of a preferred but not exclusive embodiment of surgical method according to the invention, illustrated by way of non-limiting example in the accompanying figures of the drawings, in which.

DETAILED DESCRIPTION

Figure 1:
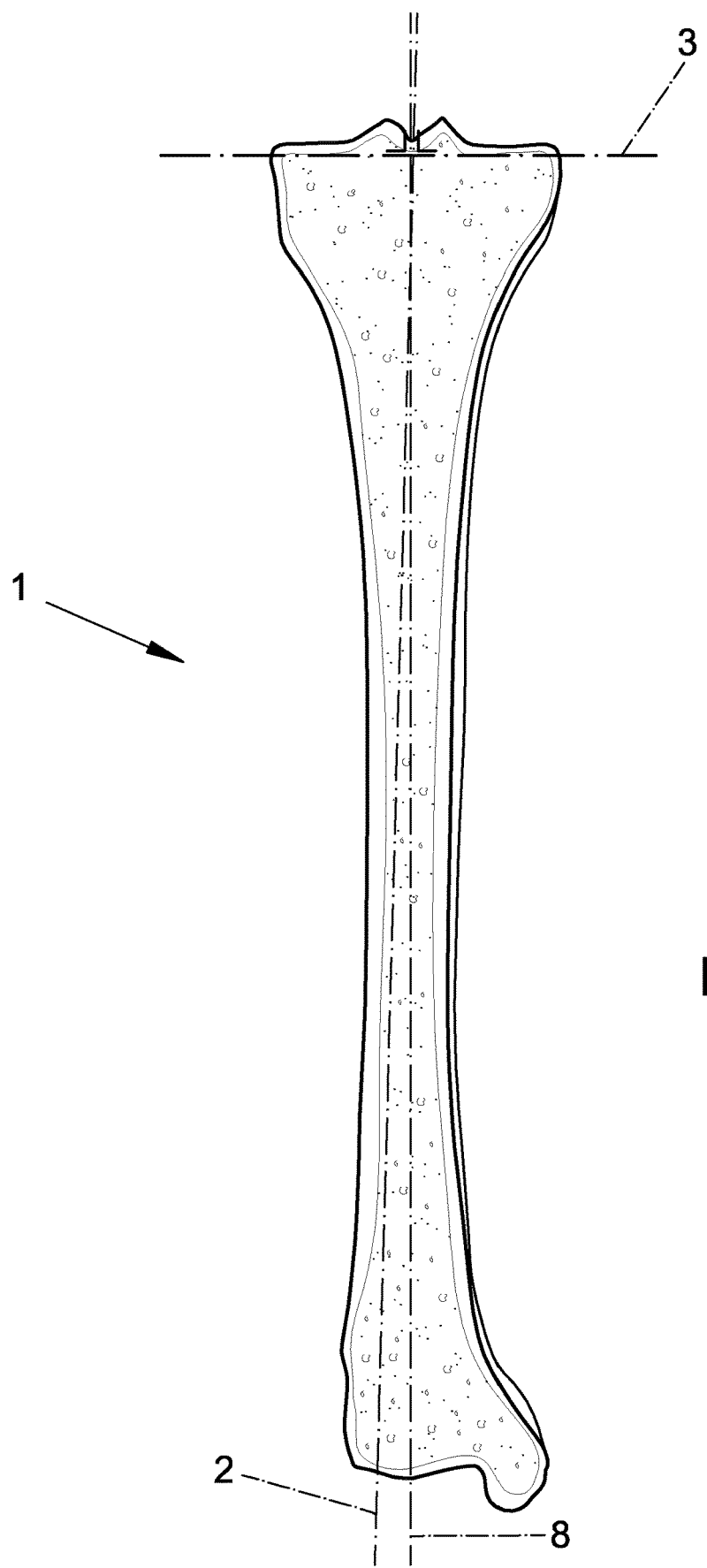
FIG. 1 is a view illustrating an exemplary image of a patient tibia with epiphysary axis and the tibial cut shown.

Although several embodiments, examples, and illustrations are disclosed below, it will be understood by those of ordinary skill in the art that the inventions described herein extend beyond the specifically disclosed embodiments, examples, and illustrations and includes other uses of the inventions and obvious modifications and equivalents thereof. Embodiments of the inventions are described with reference to the accompanying figures, wherein like numerals refer to like elements throughout. The terminology used in the description presented herein is not intended to be interpreted in any limited or restrictive manner simply because it is being used in conjunction with a detailed description of certain specific embodiments of the inventions. In addition, embodiments of the inventions can comprise several novel features and no single feature is solely responsible for its desirable attributes or is essential to practicing the inventions herein described.

Orthopedic procedures and prostheses are commonly used to repair or replace damaged bone and tissue in the human body. The purpose of prosthetic knee surgery is in fact to reduce pain and restore the function of the diseased joint.

A knee arthroplasty can be used to restore the natural function of the knee by repairing damaged or diseased joint surfaces of the femur and/or tibia.

The total knee arthroplasty involves the elimination of the cartilages damaged on the articular surfaces of the femur and tibia by means of bone preparation techniques which will host the components and the positioning of the femoral and tibial components on the two surfaces, so that they go to "Cover" the old surface. That makes the two surfaces congruent, allowing the movement of the new joint.

An aspect that is probably of great importance in the field of prostheses is represented by a correct and objective assessment of the patient's functional request, based on his work and on his functional expectations, including those of a sports-recreational type. It is therefore necessary to carefully analyze the type and quantity of the functional request to which the knee joint will be subjected, without omitting some extremely important technical details such as the angle of bending most frequently during the working and/or recreational life to which the prosthetic implant will be subjected.

Outcomes of Total Knee Arthroplasty (TKA) are limited by several factors, predominantly the insufficient reproduction of individual knee kinematics. That determines insufficient stability, particularly in mid-flexion that is the most frequent range of motion in the daily life.

Proper alignment of prosthetic component in knee replacement is an important factor in the longevity and function of the implant. Malalignment can cause wear of the implant, patient discomfort and functional limitation.

Historically, mechanical alignment technique has been considered the gold standard, however it does not restore individual morphology. A possible solution to reconstruct as much as possible the joint morphotype is represented by customized implants accurately produced on the basis of individual morphological and kinematic features.

Custom-made prosthesis manufactured with additive technologies are very flexible and permit a wide variability in implant shape and design. Additive manufacturing requires preoperative modeling based on CT/MRI 3d virtual reconstruction.

However, morphological reconstruction based only on articular surface reconstruction is not enough to guarantee the intrinsic stability and weight-bearing axis.

Therefore, success in implanting knee arthroplasty depends substantially on correct patient selection, the design of the implant chosen and of course the appropriate surgical technique.

An aim of the present invention is therefore that of providing a surgical technique which guarantee outcomes at least in the majority of the cases, excluding severe extra-articular, post-traumatic deformities and valgus severe dysplastic deformities.

The technical task, as well as these and other objects, according to the present invention are achieved by providing a surgical method for preparing a knee of a patient to implant a customized knee prosthesis comprising identifying epiphysary axis of the patient tibia by connecting the center of the tibial plateau with the center of the growth plate remnant on a preoperative planning, and performing a tibial cut perpendicular to the epiphysary axis of the tibia.

Preferably the cutting guide based on the mechanical axis of the tibia is used and the angle between the epiphysary axis and the mechanical axis of the tibia is measured to perform the tibial cut.

The invention also provide a surgical method for preparing a knee of a patient to implant a customized knee prosthesis comprising identifying the bisector axis of the trochlear groove of the patient femur on a preoperative planning and then performing the femur cut perpendicular to the bisector axis.

Preferably a cutting guide based on the mechanical axis of the femur is used and the angle between the bisector axis and mechanical axis of the femur is measured to perform the femur cut.

Finally the invention provide also for a surgical method for implanting a customized prosthesis in a knee of a patient comprising the step of identifying epiphysary axis of the patient tibia by connecting the center of the tibial plateau with the center of the growth plate remnant on a preoperative planning and then performing a tibial cut perpendicular to the epiphysary axis of the tibia, identifying the bisector axis of the trochlear groove of the patient femur on a preoperative planning and then performing the femur cut perpendicular to the bisector axis, realizing a patient specific prosthesis on the basis of the performed tibial cut and femur cut and implanting the patient specific prosthesis in the knee of the patient.

Figure 2:
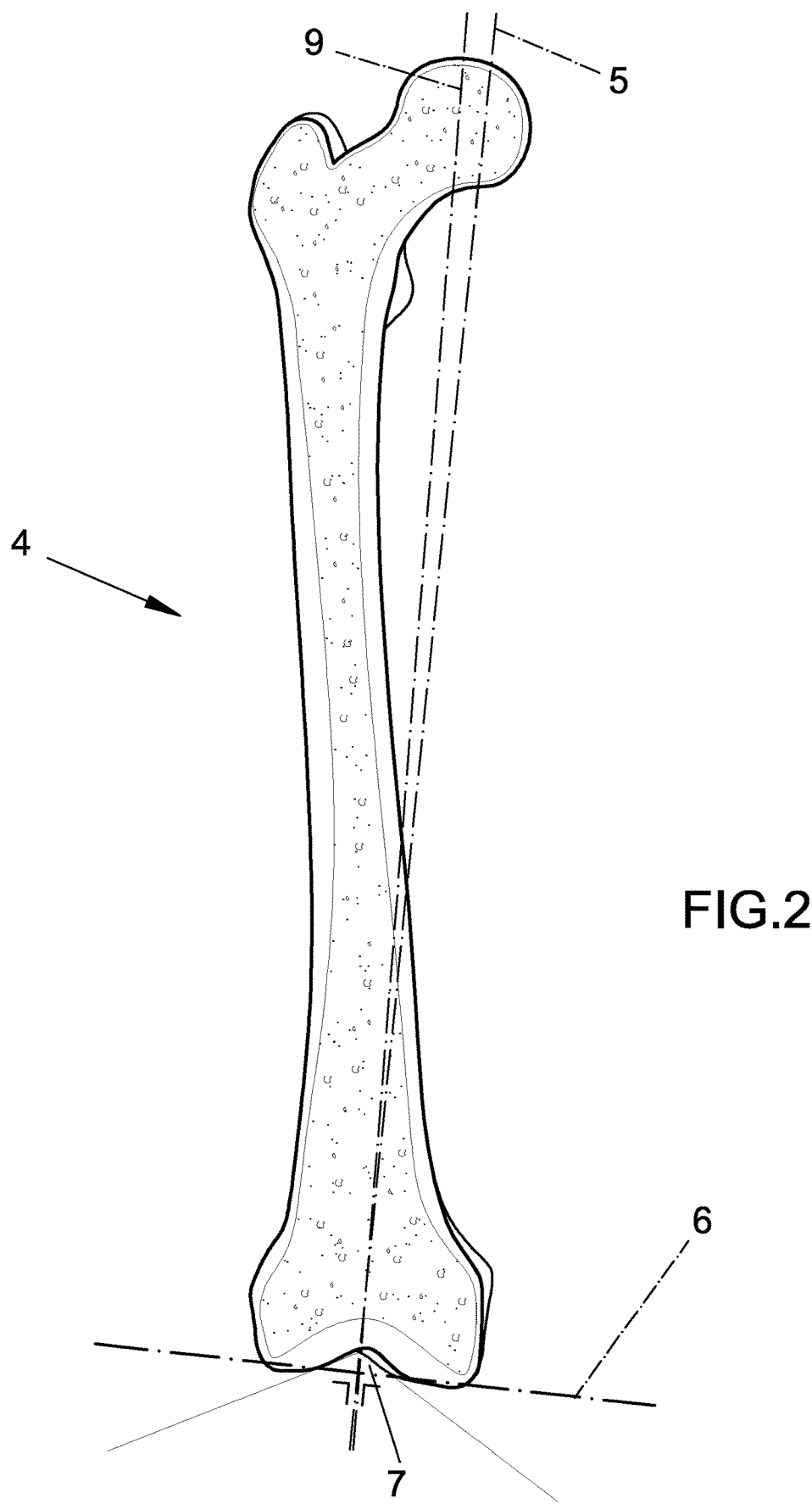
FIG. 2 is a view illustrating an exemplary image of a patient femur with bisector axis and the femur cut shown.

Further characteristics and advantages of the invention will more fully emerge from the description of a preferred but not exclusive embodiment of surgical method according to the invention, illustrated by way of non-limiting example in the accompanying figures of the drawings, in which:

FIG. 1 is a view illustrating an exemplary image of a patient tibia with epiphysary axis and the tibial cut shown; and FIG. 2 is a view illustrating an exemplary image of a patient femur with bisector axis and the femur cut shown.

According to the invention, the stability is spontaneously achieved if articular reconstruction is performed based on individual patient anatomical and kinematic features.

I Embodiment: Tibia

In a first embodiment of the invention it is provided a surgical method for preparing a knee of a patient to implant a customized knee prosthesis comprising, as a first step, the identification of epiphysary axis 2 of the patient tibia 1 on a preoperative planning, for instance through a CT scan.

Natural alignment of tibial resection is obtained by referring tibial resection to epiphysary axis which is defined by connecting the center of the tibial plateau and the center of the growth plate remnant, thus allowing to restore the native weight-bearing axis.

After having identify the epiphysary axis 2, the surgeon proceed to perform a tibial cut 3 perpendicular to the epiphysary axis 2 of the patient tibia 1.

II Embodiment: Femur

In a second embodiment of the invention it is provided a surgical method for preparing a knee of a patient to implant a customized knee prosthesis comprising, as a first step, the identification of the bisector axis 5 of the trochlear groove 7 of the patient femur 4 on a preoperative planning, for instance though a CT scan. The bisector axis is calculated as a bisector of the angle defining the trochlear groove.

After having identify the bisector axis 5, the surgeon proceed to perform a femural cut 6 perpendicular to the epiphysary axis 5 of the patient femur 4.

From a kinematical point of view two distinguished joints with different biomechanical properties can be identified in a femur:
a) The first joint includes posterior aspect of medial and lateral condyles and it is involved in range of motion between 30° and 120° of flexion. Analyzing its kinematic, a complex of instantaneous flexion axes (not corresponding to the trans-epicondylar axis) can be identified and they describe an elliptical figure, individual for each knee and depending on the patient morphotype.
In a physiological joint the natural alignment of the tibial plateau and the femoral condyles allows to easily identify the flexion axis. In an osteoarthritic joint the restoration of natural orientation of tibial plateau and the restoration of femoral condyles shape and sizes require appropriate prosthetic components and polyethylene insert to re-establish the Femoral Flexion Axis.
b) The second joint includes the anterior femoral surface that is involved in 0° to 30° range of motion. The instantaneous flexion axis becomes a rotation axis vertically oriented and corresponding approximately to the mechanical axis, thus guaranteeing the "screw home" mechanism which increases stability in extension.

The native orientation of distal femoral resection automatically balance the osteochondral loss or deformity of the distal aspect of femoral condyles. Distal femoral resection has to be perpendicular to an anatomical landmark: the bisector axis of the trochlear groove.

The alignment of the lower limb obtained with this technique corresponds in most cases to the natural mechanical alignment of the lower limb in single leg static weight-bearing position independently from varus/valgus alignment of the joint line.

Therefore, reconstructing the tibial plateau surface and the shape and dimensions of the femoral condyles, it can be restored the anatomical axis of the femur on the basis of over-all lower limb weight-bearing axis. In this way it is possible and feasible to plan an individual resurfacing surgery on the 3d virtual reconstruction of patient anatomy in order to ensure an exact ligament stability and mechanics both in extension and in flexion.

Surgical Technique

A native knee is naturally balanced. This stability is provided by the shape of the condyles and tibial plateau and by the ligaments around the knee. The degenerative changes produced by the osteoarthritis determine an osteochondral loss and production of osteophytes that alters the tension of the ligaments.

The present invention provides also a surgical method for implanting a customized prosthesis in a knee of a patient comprising the step of identifying epiphysary axis 2 of the patient tibia 1 by connecting the center of the tibial plateau with the center of the growth plate remnant on a preoperative planning and then performing a tibial cut 3 perpendicular to the epiphysary axis 2 of the tibia 1, identifying the bisector axis 5 of the trochlear groove 7 of the patient femur 4 on a preoperative planning and then performing the femur cut 6 perpendicular to the bisector axis 5, realizing a patient specific prosthesis on the basis of the performed tibial cut 3 and femur cut 6 and finally implanting the patient specific prosthesis in the knee of the patient.

Objective of the Technique

Restore the balance of the native knee that was altered by the osteoarthritic degeneration.

Tibia:

In order to reproduce the native tibia, the cut 3 must be performed perpendicular to the epiphysary axis. This axis is obtained connecting the center of the tibial plateau with the center of the of the growth plate remnant. Cutting guides and smart cutting guides are based on the mechanical axis 8 of the tibia 1; therefore to perform a cut 3 perpendicular to the epiphysary axis 2 it sufficient to measure the angle between this axis 2 and the mechanical axis 8 of the tibia 1 on the preoperative planning.

Femur:

Distal cut 6: this cut 6 has to be perpendicular to the bisector 5 of the trochlear groove 7. This line is to be determined preoperatively on CT scans. Cutting guides and smart cutting guides are based on the mechanical axis 9 of the femur 4; therefore to perform a cut 6 perpendicular to the bisector 5 of the trochlear groove 7 axis it sufficient to measure the angle between this axis 5 and the mechanical axis 9 of the femur 4 on the preoperative planning.

Normally the posterior condyles are not interested by degeneration therefore it is sufficient to remove the amount of bone and cartilage corresponding to the thickness of the implant without major corrections and restoring in this simple way the correct position of the instantaneous axis of flexion.

This surgical technique is conceived to guarantee outcomes at least in the majority of the cases, excluding severe extra-articular, post-traumatic deformities and valgus severe dysplastic deformities.

Although this invention has been disclosed in the context of certain embodiments and examples, it will be understood by those skilled in the art that the invention extends beyond the specifically disclosed embodiments to other alternative embodiments and/or uses of the invention and obvious modifications and equivalents thereof. In addition, while several variations of the embodiments of the invention have been shown and described in detail, other modifications, which are within the scope of this invention, will be readily apparent to those of skill in the art based upon this disclosure. It is also contemplated that various combinations or sub-combinations of the specific features and aspects of the embodiments may be made and still fall within the scope of the invention. It should be understood that various features and aspects of the disclosed embodiments can be combined with, or substituted for, one another in order to form varying modes of the embodiments of the disclosed invention. Any methods disclosed herein need not be performed in the order recited. Thus, it is intended that the scope of the invention herein disclosed should not be limited by the particular embodiments described above.

Conditional language, such as, among others, "can," "could," "might," or "may," unless specifically stated otherwise, or otherwise understood within the context as used, is generally intended to convey that certain embodiments include, while other embodiments do not include, certain features, elements and/or steps. Thus, such conditional language is not generally intended to imply that features, elements and/or steps are in any way required for one or more embodiments or that one or more embodiments necessarily include logic for deciding, with or without user input or prompting, whether these features, elements and/or steps are included or are to be performed in any particular embodiment. The headings used herein are for the convenience of the reader only and are not meant to limit the scope of the inventions or claims.

Further, while the methods and devices described herein may be susceptible to various modifications and alternative forms, specific examples thereof have been shown in the drawings and are herein described in detail. It should be understood, however, that the invention is not to be limited to the particular forms or methods disclosed, but, to the contrary, the invention is to cover all modifications, equivalents, and alternatives falling within the spirit and scope of the various implementations described and the appended claims. Further, the disclosure herein of any particular feature, aspect, method, property, characteristic, quality, attribute, element, or the like in connection with an implementation or embodiment can be used in all other implementations or embodiments set forth herein. Any methods disclosed herein need not be performed in the order recited. The methods disclosed herein may include certain actions taken by a practitioner; however, the methods can also include any third-party instruction of those actions, either expressly or by implication. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers and should be interpreted based on the circumstances (e.g., as accurate as reasonably possible under the circumstances, for example ±5%, ±10%, ±15%, etc.). For example, "about 3.5 mm" includes "3.5 mm." Phrases preceded by a term such as "substantially" include the recited phrase and should be interpreted based on the circumstances (e.g., as much as reasonably possible under the circumstances). For example, "substantially constant" includes "constant." Unless stated otherwise, all measurements are at standard conditions including temperature and pressure.

As used herein, a phrase referring to "at least one of" a list of items refers to any combination of those items, including single members. As an example, "at least one of: A, B, or C" is intended to cover: A, B, C, A and B, A and C, B and C, and A, B, and C. Conjunctive language such as the phrase "at least one of X, Y and Z," unless specifically stated otherwise, is otherwise understood with the context as used in general to convey that an item, term, etc. may be at least one of X, Y or Z. Thus, such conjunctive language is not generally intended to imply that certain embodiments require at least one of X, at least one of Y, and at least one of Z to each be present.

What is claimed is:

1. A surgical method for implanting a customized prosthesis in a knee of a patient comprising the steps of:

identifying epiphysary axis of the patient tibia by connecting the center of the tibial plateau with the center of the growth plate remnant on a preoperative planning and then performing a tibial cut perpendicular to the epiphysary axis of the tibia;

identifying the bisector axis of the trochlear groove of the patient femur on a preoperative planning and then performing the femur cut perpendicular to the bisector axis;

realizing a patient specific prosthesis on the basis of the performed tibial cut and femur cut; and implanting the patient specific prosthesis in the knee of the patient.

* * * * *